United States Patent
Mitchell

(10) Patent No.: US 11,529,297 B2
(45) Date of Patent: Dec. 20, 2022

(54) SKINCARE COMPOSITIONS INCLUDING ZINC OXIDE

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Fort Worth, TX (US)

( * ) Notice: Subject to any disclaimer, the term of this patent is extended or adjusted under 35 U.S.C. 154(b) by 51 days.

(21) Appl. No.: 17/154,842

(22) Filed: Jan. 21, 2021

(65) Prior Publication Data
US 2022/0226211 A1    Jul. 21, 2022

(51) Int. Cl.
| | | |
|---|---|---|
| *A61K 8/27* | (2006.01) | |
| *A61K 8/92* | (2006.01) | |
| *A61K 8/34* | (2006.01) | |
| *A61K 8/37* | (2006.01) | |
| *A61K 8/41* | (2006.01) | |
| *A61K 8/891* | (2006.01) | |
| *A61K 8/81* | (2006.01) | |
| *A61K 8/06* | (2006.01) | |
| *A61Q 19/00* | (2006.01) | |
| *A61K 8/86* | (2006.01) | |

(52) U.S. Cl.
CPC ............... *A61K 8/27* (2013.01); *A61K 8/062* (2013.01); *A61K 8/342* (2013.01); *A61K 8/345* (2013.01); *A61K 8/375* (2013.01); *A61K 8/41* (2013.01); *A61K 8/8152* (2013.01); *A61K 8/8158* (2013.01); *A61K 8/86* (2013.01); *A61K 8/891* (2013.01); *A61K 8/922* (2013.01); *A61Q 19/005* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 10,668,010 B2* | 6/2020 | Ficko | ............... | A61Q 17/04 |
| 2010/0136148 A1* | 6/2010 | Saint Victor | ............ | C11D 3/48 |
| | | | | 424/754 |
| 2018/0133126 A1* | 5/2018 | Alspaugh, II | .......... | A61K 8/496 |

OTHER PUBLICATIONS

Drugs.com "COZIMA," last updated May 12, 2020; https://www.drugs.com/otc/1185133/cozima.html (Year: 2020).*

* cited by examiner

*Primary Examiner* — David J Blanchard
*Assistant Examiner* — Alissa Prosser
(74) *Attorney, Agent, or Firm* — Winstead PC

(57) ABSTRACT

In an embodiment, the present disclosure relates to a composition for treating or preventing a skin condition. In some embodiments, the composition includes zinc oxide with a concentration between about 5 and 30 wt/wt %, coconut oil with a concentration between about 0.1 and 5 wt/wt %, tea tree oil with a concentration between about 0.00025 and 0.1 wt/wt %, citronella oil with a concentration between about 0.00025 and 0.1 wt/wt %, and lemongrass oil with a concentration between about 0.01 and 1 wt/wt %. In a further embodiment, the present disclosure pertains to a composition for treating or preventing a skin condition including zinc oxide with a concentration of about 24 wt/wt %, coconut oil with a concentration of about 1 wt/wt %, tea tree oil with a concentration of about 0.001 wt/wt %, citronella oil with a concentration of about 0.001 wt/wt %, and lemongrass oil with a concentration of about 0.08 wt/wt %.

18 Claims, No Drawings

SKINCARE COMPOSITIONS INCLUDING ZINC OXIDE

TECHNICAL FIELD

The present disclosure relates generally to skin care compositions and more particularly, but not by way of limitation, to skincare compositions including zinc oxide.

BACKGROUND

This section provides background information to facilitate a better understanding of the various aspects of the disclosure. It should be understood that the statements in this section of this document are to be read in this light, and not as admissions of prior art.

Diaper rash is a common form of inflamed skin (dermatitis) that appears as a patchwork of red skin where the diaper is in constant contact with skin. Generally, diaper rash is related to wet or infrequently changed diapers, skin sensitivity, or chafing, and usually affects babies, though anyone who wears diapers regularly can develop diaper rash. Typically, diaper rash is identified by red, tender-looking skin in the buttock, thigh, and genital regions. A child or an adult wearer of diapers may appear more uncomfortable than normal (especially during diaper changes) as the irritated skin is an annoyance to the wearer. Discomfort is generally more prone when the inflamed area is washed or touched. Diaper rash can clear up via air-drying; however, ointments or creams generally provide more immediate relief. As such, various embodiments of the present disclosure are directed towards skin care compositions to ease symptoms and treat or prevent diaper rash.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure relates to a composition for treating or preventing a skin condition. In some embodiments, the composition includes zinc oxide with a concentration between about 5 and 30 wt/wt %, coconut oil with a concentration between about 0.1 and 5 wt/wt %, tea tree oil with a concentration between about 0.00025 and 0.1 wt/wt %, citronella oil with a concentration between about 0.00025 and 0.1 wt/wt %, and lemongrass oil with a concentration between about 0.01 and 1 wt/wt %.

In a further embodiment, the present disclosure pertains to a composition for treating or preventing a skin condition including zinc oxide with a concentration of about 24 wt/wt %, coconut oil with a concentration of about 1 wt/wt %, tea tree oil with a concentration of about 0.001 wt/wt %, citronella oil with a concentration of about 0.001 wt/wt %, and lemongrass oil with a concentration of about 0.08 wt/wt %.

In an additional embodiment, the present disclosure pertains to a composition for treating or preventing a skin condition including zinc oxide with a concentration of about 24 wt/wt %, coconut oil with a concentration of about 1 wt/wt %, tea tree oil with a concentration of about 0.001 wt/wt %, citronella oil with a concentration of about 0.001 wt/wt %, lemongrass oil with a concentration of about 0.08 wt/wt %, purified water with a concentration of about 40.418 wt/wt %, disodium EDTA with a concentration of about 6 wt/wt %, glycerin with a concentration of about 2 wt/wt %, an acrylates/acrylamide copolymer, mineral oil, polysorbate 85 composition with a concentration of about 3 wt/wt %, propylene glycol stearate with a concentration of about 2.5 wt/wt %, dimethicone with a concentration of about 6.9 wt/wt %, octyldodecanol with a concentration of about 2 wt/wt %, isopropyl myristate with a concentration of about 3 wt/wt %, an oil-in-water emulsifier with a concentration of about 4 wt/wt %, polyethylene glycol (PEG)-20 methyl glucose sesquistearate with a concentration of about 1.5 wt/wt %, and stearyl alcohol with a concentration of about 3.6 wt/wt %.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

At least half of all babies get a diaper rash at some point. Reddened and inflamed skin in the diaper area is one of the most common reasons parents seek medical care for their child. Diaper rash effects babies, toddlers, and adults, and many factors can cause diaper rash. For example, prolonged exposure to urine or stool can irritate skin, especially sensitive skin. A diaper wearer, such as a baby, can be more prone to diaper rash if they experience frequent bowel movements or diarrhea, as feces is much more irritating to the skin than urine. Additionally, tight fitting diapers or clothing that continually rub against the skin can lead to a rash, and when exposed to urine or stool can develop into diaper rash. In addition, skin may also react to various types or brands of cleaning wipes, various types or brands of disposable diapers, or types or brands of detergents, bleaches or fabric softeners used to launder cloth diapers. Moreover, ingredients found in various lotions, powders, or oils can further exacerbate diaper rash symptoms, or cause diaper rash when used on sensitive skin. Furthermore, bacterial or fungal infections, such as yeast infections, can also play a role in the development of diaper rash. Even a simple skin infection may spread to the surrounding regions covered by a diaper (e.g., buttock, thighs, and genitals), which are especially vulnerable because these areas are generally warm and moist, making them a breeding ground for bacteria and fungus. Generally, these rashes can be found within the creases of the skin and may exhibit red dots scattered around the creases.

Furthermore, sensitive skin can be especially susceptible to diaper rash. Diaper wearers with skin conditions, such as atopic dermatitis or seborrheic dermatitis (i.e., eczema), are more likely to develop diaper rash. While these particular skin conditions primarily affect and irritate other regions of the body, they can never the less migrate to, or develop on or near, areas covered by a diaper. These skin conditions can increase the likelihood of diaper rash or cause diaper symptoms to be more severe.

In addition, with children, the introduction of new foods can become a source of diaper rash. As babies start to eat solid foods, generally their stool content changes. This change in stool content can increase the likelihood of diaper rash. Often, changes in diet also increase the frequency of stools, which as discussed above, can lead to diaper rash. Moreover, if a baby is breast-fed, they may develop diaper rash in response to something the mother has eaten.

Even use of various types of medications used to treat infections can promote the development of diaper rash. For instance, the use of antibiotics used to kill bacteria can increase the likelihood of diaper rash development. Antibiotics kill bacteria, often indiscriminately—this means that antibiotics generally kill good bacterial while also killing bad bacteria. This can pose a problem as good bacteria generally prevents various types of fungal infections, such as yeast infections. As the amount of good bacteria in the diaper region is depleted, there is an increased chance of developing diaper rash caused by a yeast infection. This also means that breast-fed babies whose mothers take antibiotics are also at an increased risk of developing diaper rash. Moreover, antibiotic usage has been linked to an increase in chances of developing diarrhea, which leaves the diaper region prone to diaper rash, as discussed above.

Since diaper rash is very common among diaper wearers, and many different factors can cause diaper rash, treatment of diaper rash quickly and efficiently is highly desirable. Various compounds, in addition to oils and plant extracts can be used to treat and alleviate symptoms of diaper rash, and protect chafed skin due to diaper rash while also sealing out wetness. For instance, compounds such as zinc oxide can be utilized as a skin protectant, both to treat and alleviate diaper rash and its symptoms, and furthermore, to prevent diaper rash. Topical zinc oxide can be utilized to treat and prevent minor skin irritations associated with diaper rash, burns, cuts, allergic reactions, and insect bites. Zinc oxide works by forming a barrier on top of the skin that protects the area from moisture and other irritants. While zinc oxide is effective in protecting the skin from irritants and moisture, additional components are typically necessary to further ease symptoms or treat diaper rash. Thus, it is advantageous to utilize other components to aid in the healing of diaper rash. As zinc oxide forms a barrier on the skin, generally components need to be integrated in topical zinc oxide treatments.

Because diaper rash causes skin irritation, in addition to preventing irritants from coming in contact with an infected area of skin, various components that exhibit antibacterial, antifungal, and anti-inflammatory effects is greatly desired. In addition to general components to prevent infection and reduce inflammation, moisturizing the affected area can also be desirable when utilizing various antibacterial, antifungal, and anti-inflammatory agents which can sometimes lead to over-drying skin. Coconut oil is naturally antibacterial, antifungal, and moisturizing. Coconut oil is composed of a unique combination of natural fats which contribute to its effects on treating the skin. Coconut oil contains the fatty acid linoleic acid which is beneficial for irritated and inflamed skin, and lauric acid which is both hydrating and antimicrobial. Studies indicate that coconut oil improves skin barrier function and repair, has antibacterial and anti-inflammatory properties, and is an effective moisturizer.

Further, diaper rash treatments can prove beneficial by leveraging the use of pain relief, antiseptic, antibacterial, antifungal, and anti-inflammatory agents to reduce pain, itching or swelling, or infections and wounds related to diaper rash. Citronella oil is an oil that is sourced from the distillation of Asian grass plants from the Cymbopogon genus. Studies have found that citronella oil has the ability to destroy cell walls of fungus and kill organisms within the cells that cause infection. This indicates that citronella oil has the potential to be used as a fungicide. Moreover, antifungal and anti-inflammatory properties of citronella oil assist in the healing of damaged skin caused by diaper rash.

Similar to citronella oil, both lemongrass oil and tea tree oil have anti-inflammatory properties thereby aiding in pain relief caused by inflammation due to diaper rash. In addition to providing relief from inflammation and pain, lemongrass oil and tea tree oil further act as antibacterial and antifungal agents. Thus, lemongrass oil and tea tree oil can be used to prevent bacterial or fungal infections on the skin related to irritated or damaged skin caused by diaper rash. As such, lemongrass oil and tea tree oil provide the advantages of reducing risk of bacterial or fungal infections by acting as an antiseptic and reducing pain related to inflammation of damaged skin.

In addition to the above-mentioned components, various other constituents can be present within diaper rash creams to enhance both efficacy and provide for a more robust and easy to use formulation. For example, various thickeners can be added to the formulation for ease of use (e.g., forming a cream formulation). Emollients, spreading agents, emulsifiers, solubilizers, and the like, such as isopropyl myristate can additionally be added to the formulation to provide for softening or soothing of skin, or to provide better absorption into the skin. Similar to emollients, additional moisturizers or vitamins (e.g., vitamin E) can also be added to moisturize and/or lubricate the skin an area of skin showing signs of diaper rash. Various other constituents that are well known to those of ordinary skill in the art are also readily envisioned to provide for ease of handling, formulation consistency, dilution, pH balance/buffering, and the like.

In addition to diaper rash, compositions that are utilized to treat and prevent diaper rash are not limited solely to diaper rash. For instance, the compositions as described above relative to diaper rash can be used to treat many skin conditions that affect people of all ages. For example, the compositions disclosed herein can be utilized in healing sores, rashes, and other various skin diseases. Zinc, in combination with coconut oil, citronella oil, lemongrass oil, and tea tree oil have a wide range of healing properties. In some instances, the compositions disclosed herein can prevent and treat rash caused by adult incontinence, various forms of diaper rashes, skin rashes, irritated skin, and combinations of the same and like, Reference will now be made to more specific embodiments of the present disclosure and data that provides support for such embodiments. However, it should be noted that the disclosure below is for illustrative purposes only and is not intended to limit the scope of the claimed subject matter in any way.

Table 1, shown below, is an example diaper rash cream formulation according to aspects of the present disclosure.

TABLE 1

Diaper Rash Cream Formulation.

| Ingredients | Amount (% w/w) |
| --- | --- |
| Zinc Oxide | 24.0 |
| Purified Water, USP | 40.418 |
| Disodium EDTA | 6.0 |
| Glycerin | 2.0 |
| Acrylates/Acrylamide Copolymer, Mineral Oil, Polysorbate 85 (NOVEMER ™ EC-1) | 3.0 |
| Propylene Glycol Stearate | 2.5 |
| Dimethicone | 6.9 |

TABLE 1-continued

Diaper Rash Cream Formulation.

| Ingredients | Amount (% w/w) |
| --- | --- |
| Octyldodecanol (EUTANOL ® G) | 2.0 |
| Isopropyl Myristate | 3.0 |
| Oil-in-Water Emulsifier (EMULGIN ® B25) | 4.0 |
| Polyethylene Glycol (PEG)-20 Methyl Glucose Sesquistearate | 1.5 |
| Stearyl Alcohol (LANETTE ® 18) | 3.6 |
| Coconut Oil | 1.0 |
| Tea Tree Oil | 0.001 |
| Citronella Oil | 0.001 |
| Lemongrass Oil | 0.080 |

In some embodiments, the zinc oxide has a concentration between about 5 and 30 wt/wt %. In some embodiments, the purified water has a concentration between about 10 and 50 wt/wt %. In some embodiments, the disodium EDTA has a concentration between about 1 and 8 wt/wt %. In some embodiments, the glycerin has a concentration between about 0.5 and 5 wt/wt %. In some embodiments, the acrylates/acrylamide copolymer, mineral oil, polysorbate 85 has a concentration between about 0.5 and 5 wt/wt %. In some embodiments, the acrylates/acrylamide copolymer, mineral oil, polysorbate 85 is NOVEMER™ EC-1. In some embodiments, the propylene glycol stearate has a concentration between about 0.5 and 5 wt/wt %. In some embodiments, the dimethicone has a concentration between about 1 and 10 wt/wt %. In some embodiments, the octyldodecanol has a concentration between about 0.1 and 5 wt/wt %. In some embodiments, the octyldodecanol is EUTANOL® G. In some embodiments, the isopropyl myristate has a concentration between about 0.5 and 5 wt/wt %. In some embodiments, the oil-in-water emulsifier has a concentration between about 1 and 5 wt/wt %. In some embodiments, the oil-in-water emulsifier is EMULGIN® B25. In some embodiments, the PEG-20 methyl glucose sesquistearate has a concentration between about 0.1 and 5 wt/wt %. In some embodiments, the stearyl alcohol has a concentration between about 0.1 and 5 wt/wt %. In some embodiments, the stearyl alcohol is LANETTE® 18.

In some embodiments, the coconut oil has a concentration between about 0.1 and 5 wt/wt %. In some embodiments, the tea tree oil has a concentration between about 0.00025 and 0.1 wt/wt %. In some embodiments, the citronella oil has a concentration between about 0.00025 and 0.1 wt/wt %. In some embodiments, the lemongrass oil has a concentration between about 0.01 and 1 wt/wt %.

In some embodiments, the zinc oxide has a concentration of about 24 wt/wt %. In some embodiments, the purified water has a concentration of about 40.418 wt/wt %. In some embodiments, the disodium EDTA has a concentration of about 6 wt/wt %. In some embodiments, the glycerin has a concentration of about 2 wt/wt %. In some embodiments, the acrylates/acrylamide copolymer, mineral oil, polysorbate 85 has a concentration of about 3 wt/wt %. In some embodiments, the acrylates/acrylamide copolymer, mineral oil, polysorbate 85 is NOVEMER™ EC-1. In some embodiments, the propylene glycol stearate has a concentration of about 2.5 wt/wt %. In some embodiments, the dimethicone has a concentration of about 6.9 wt/wt %. In some embodiments, the octyldodecanol has a concentration of about 2 wt/wt %. In some embodiments, the octyldodecanol is EUTANOL® G. In some embodiments, the isopropyl myristate has a concentration of about 3 wt/wt %. In some embodiments, the oil-in-water emulsifier has a concentration of about 4 wt/wt %. In some embodiments, the oil-in-water emulsifier is EMULGIN® B25. In some embodiments, the PEG-20 methyl glucose sesquistearate has a concentration of about 1.5 wt/wt %. In some embodiments, the stearyl alcohol has a concentration of about 3.6 wt/wt %. In some embodiments, the stearyl alcohol is LANETTE® 18.

In some embodiments, the coconut oil has a concentration of about 1 wt/wt %. In some embodiments, the tea tree oil has a concentration of about 0.001 wt/wt %. In some embodiments, the citronella oil has a concentration of about 0.001 wt/wt %. In some embodiments, the lemongrass oil has a concentration of about 0.08 wt/wt %.

As disclosed in further detail herein, in an embodiment, the present disclosure relates to a composition for treating or preventing a skin condition. In some embodiments, the composition includes zinc oxide with a concentration between about 5 and 30 wt/wt %, coconut oil with a concentration between about 0.1 and 5 wt/wt %, tea tree oil with a concentration between about 0.00025 and 0.1 wt/wt %, citronella oil with a concentration between about 0.00025 and 0.1 wt/wt %, and lemongrass oil with a concentration between about 0.01 and 1 wt/wt %.

In some embodiments, the zinc oxide has a concentration of about 24 wt/wt %. In some embodiments, the coconut oil has a concentration of about 1 wt/wt %. In some embodiments, the tea tree oil has a concentration of about 0.001 wt/wt %. In some embodiments, the citronella oil has a concentration of about 0.001 wt/wt %. In some embodiments, the lemongrass oil has a concentration of about 0.08 wt/wt %.

In some embodiments, the composition further includes purified water with a concentration between about 10 and 50 wt/wt %, disodium EDTA with a concentration between about 1 and 8 wt/wt %, glycerin with a concentration between about 0.5 and 5 wt/wt %, an acrylates/acrylamide copolymer, mineral oil, polysorbate 85 composition with a concentration between about 0.5 and 5 wt/wt %, propylene glycol stearate with a concentration between about 0.5 and 5 wt/wt %, dimethicone with a concentration between about 1 and 10 wt/wt %, octyldodecanol with a concentration between about 0.1 and 5 wt/wt %, isopropyl myristate with a concentration between about 0.5 and 5 wt/wt %, an oil-in-water emulsifier with a concentration between about 1 and 5 wt/wt %, PEG-20 methyl glucose sesquistearate with a concentration between about 0.1 and 5 wt/wt %, and stearyl alcohol with a concentration between about 0.1 and 5 wt/wt %.

In some embodiments, the purified water has a concentration of about 40.418 wt/wt %. In some embodiments, the disodium EDTA has a concentration of about 6 wt/wt %. In some embodiments, the glycerin has a concentration of about 2 wt/wt %. In some embodiments, the acrylates/acrylamide copolymer, mineral oil, polysorbate 85 composition has a concentration of about 3 wt/wt %. In some embodiments, the propylene glycol stearate has a concentration of about 2.5 wt/wt %. In some embodiments, the dimethicone has a concentration of about 6.9 wt/wt %. In some embodiments, the octyldodecanol has a concentration of about 2 wt/wt %. In some embodiments, the isopropyl myristate has a concentration of about 3 wt/wt %. In some embodiments, the oil-in-water emulsifier has a concentration of about 4 wt/wt %. In some embodiments, the PEG-20 methyl glucose sesquistearate has a concentration of about 1.5 wt/wt %. In some embodiments, the stearyl alcohol has a concentration of about 3.6 wt/wt %.

In a further embodiment, the present disclosure pertains to a composition for treating or preventing a skin condition including zinc oxide with a concentration of about 24 wt/wt %, coconut oil with a concentration of about 1 wt/wt %, tea tree oil with a concentration of about 0.001 wt/wt %, citronella oil with a concentration of about 0.001 wt/wt %, and lemongrass oil with a concentration of about 0.08 wt/wt %.

In an additional embodiment, the present disclosure pertains to composition for treating or preventing a skin condition including zinc oxide with a concentration of about 24 wt/wt %, coconut oil with a concentration of about 1 wt/wt %, tea tree oil with a concentration of about 0.001 wt/wt %, citronella oil with a concentration of about 0.001 wt/wt %, lemongrass oil with a concentration of about 0.08 wt/wt %, purified water with a concentration of about 40.418 wt/wt %, disodium EDTA with a concentration of about 6 wt/wt %, glycerin with a concentration of about 2 wt/wt %, an acrylates/acrylamide copolymer, mineral oil, polysorbate 85 composition with a concentration of about 3 wt/wt %, propylene glycol stearate with a concentration of about 2.5 wt/wt %, dimethicone with a concentration of about 6.9 wt/wt %, octyldodecanol with a concentration of about 2 wt/wt %, isopropyl myristate with a concentration of about 3 wt/wt %, an oil-in-water emulsifier with a concentration of about 4 wt/wt %, PEG-20 methyl glucose sesquistearate with a concentration of about 1.5 wt/wt %, and stearyl alcohol with a concentration of about 3.6 wt/wt %.

Although various embodiments of the present disclosure have been described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A composition for treating or preventing a skin condition, the composition comprising:
   zinc oxide with a concentration between 5 and 30 wt/wt %;
   coconut oil with a concentration between 0.1 and 5 wt/wt %;
   tea tree oil with a concentration between 0.00025 and 0.1 wt/wt %;
   citronella oil with a concentration between 0.00025 and 0.1 wt/wt %;
   lemongrass oil with a concentration between 0.01 and 1 wt/wt %;
   purified water with a concentration between 10 and 50 wt/wt %;
   disodium EDTA with a concentration between 1 and 8 wt/wt %;
   glycerin with a concentration between 0.5 and 5 wt/wt %;
   an acrylates/acrylamide copolymer, mineral oil, polysorbate 85 composition with a concentration between 0.5 and 5 wt/wt %;
   propylene glycol stearate with a concentration between 0.5 and 5 wt/wt %;
   dimethicone with a concentration between 1 and 10 wt/wt %;
   octyldodecanol with a concentration between 0.1 and 5 wt/wt %;
   isopropyl myristate with a concentration between 0.5 and 5 wt/wt %;
   an oil-in-water emulsifier with a concentration between 1 and 5 wt/wt %;
   polyethylene glycol (PEG)-20 methyl glucose sesquistearate with a concentration between 0.1 and 5 wt/wt %; and
   stearyl alcohol with a concentration between 0.1 and 5 wt/wt %.

2. The composition of claim 1, wherein the zinc oxide has a concentration of 24 wt/wt %.

3. The composition of claim 1, wherein the coconut oil has a concentration of 1 wt/wt %.

4. The composition of claim 1, wherein the tea tree oil has a concentration of 0.001 wt/wt %.

5. The composition of claim 1, wherein the citronella oil has a concentration of 0.001 wt/wt %.

6. The composition of claim 1, wherein the lemongrass oil has a concentration of 0.08 wt/wt %.

7. The composition of claim 1, wherein the purified water has a concentration of 40.418 wt/wt %.

8. The composition of claim 1, wherein the disodium EDTA has a concentration of 6 wt/wt %.

9. The composition of claim 1, wherein the glycerin has a concentration of 2 wt/wt %.

10. The composition of claim 1, wherein the acrylates/acrylamide copolymer, mineral oil, polysorbate 85 composition has a concentration of 3 wt/wt %.

11. The composition of claim 1, wherein the propylene glycol stearate has a concentration of 2.5 wt/wt %.

12. The composition of claim 1, wherein the dimethicone has a concentration of 6.9 wt/wt %.

13. The composition of claim 1, wherein the octyldodecanol has a concentration of 2 wt/wt %.

14. The composition of claim 1, wherein the isopropyl myristate has a concentration of 3 wt/wt %.

15. The composition of claim 1, wherein the oil-in-water emulsifier has a concentration of 4 wt/wt %.

16. The composition of claim 1, wherein the PEG-20 methyl glucose sesquistearate has a concentration of 1.5 wt/wt %.

17. The composition of claim 1, wherein the stearyl alcohol has a concentration of 3.6 wt/wt %.

18. A composition for treating or preventing a skin condition, the composition consisting of:

zinc oxide with a concentration of 24 wt/wt %;
coconut oil with a concentration of 1 wt/wt %;
tea tree oil with a concentration of 0.001 wt/wt %;
citronella oil with a concentration of 0.001 wt/wt %;
lemongrass oil with a concentration of 0.08 wt/wt %;
purified water with a concentration of 40.418 wt/wt %;
disodium EDTA with a concentration of 6 wt/wt %;
glycerin with a concentration of 2 wt/wt %;
an acrylates/acrylamide copolymer, mineral oil, polysorbate 85 composition with a concentration of 3 wt/wt %;
propylene glycol stearate with a concentration of 2.5 wt/wt %;
dimethicone with a concentration of 6.9 wt/wt %;
octyldodecanol with a concentration of 2 wt/wt %;
isopropyl myristate with a concentration of 3 wt/wt %;
an oil-in-water emulsifier with a concentration of 4 wt/wt %;
polyethylene glycol (PEG)-20 methyl glucose sesquistearate with a concentration of 1.5 wt/wt %; and
stearyl alcohol with a concentration of 3.6 wt/wt %.

\* \* \* \* \*